Figure 1:
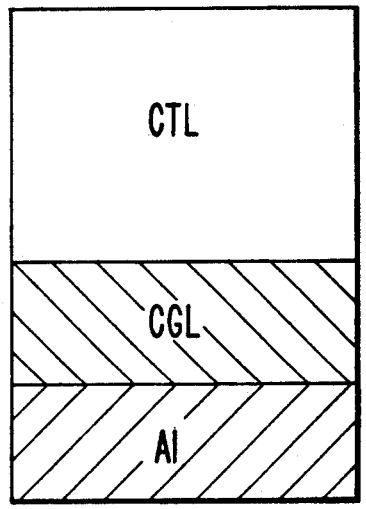

United States Patent [19]

Mizuguchi et al.

[11] Patent Number: 5,098,810

[45] Date of Patent: Mar. 24, 1992

[54] ELECTROPHOTOGRAPHIC PHOTORECEPTORS

[75] Inventors: Jin Mizuguchi, Fribourg, Switzerland; Seiji Homma, Kawanishi, Japan; Hiroshi Yamamoto, Ikeda, Japan; Takashi Deno, Takarazuka, Japan

[73] Assignee: Japat Ltd., Basel, Switzerland

[21] Appl. No.: 528,190

[22] Filed: May 24, 1990

[30] Foreign Application Priority Data

May 27, 1989 [GB] United Kingdom ............... 8912279

[51] Int. Cl.⁵ ............................................. G03G 5/06
[52] U.S. Cl. ....................................... 430/78; 430/58; 430/59; 430/83
[58] Field of Search ..................... 430/59, 58, 76, 78, 430/83

[56] References Cited

U.S. PATENT DOCUMENTS

| | | | |
|---|---|---|---|
| 4,150,987 | 4/1979 | Anderson et al. | 96/1.5 R |
| 4,278,746 | 7/1981 | Goto et al. | 430/59 |
| 4,387,147 | 6/1983 | Sakai | 430/58 |
| 4,436,800 | 3/1984 | Ohta et al. | 430/59 |
| 4,632,893 | 12/1986 | Rochat et al. | 430/58 |
| 4,760,151 | 7/1988 | Rochat et al. | 548/453 |
| 4,808,505 | 2/1989 | Ueda | 430/83 |
| 4,925,759 | 5/1990 | Hanatani et al. | 430/59 |

FOREIGN PATENT DOCUMENTS

| | | |
|---|---|---|
| 0099552 | 2/1984 | European Pat. Off. |
| 59-114545 | 7/1984 | Japan |
| 60-162260 | 8/1985 | Japan |
| 63-95457 | 4/1988 | Japan |
| 2153378 | 8/1985 | United Kingdom |

OTHER PUBLICATIONS

Patent Abstracts of Japan, vol. 10, No. 330 (p-514) (2386) Nov. 11, 1986, Abstracting JP-A-61 134 767.
Mizuguchi et al., Journal of Imaging Science, vol. 32, No. 3, Jun. 1988, pp. 135-140.
Patent Abstracts of Japan, vol. 12, No. 216 (P-719) (3063) Jun. 21, 1988, Abstracting JP-A-63 14 154.
Patent Abstracts of Japan, vol. 11, No. 389 (P-648) (2836) Dec. 19, 1987, Abstracting JP-A-62 153 959.
Tiedje et al., Solar Cells, 2 (1980), pp. 301-318.
Mitsubishi Paper Mills, Chem. Abstr. vol. 102 (1985), p. 641, Abstracting JP59-114545.
Ricoh Co., Chem. Abstr. vol. 102 (1985), p. 595, Abstracting JP59-228652.
Ota et al., Chem. Abstr. vol. 104 (1986), p. 495, Abstracting JP60-151645.
Higawara et al., Chem. Abstr. vol. 104 (1986), p. 667, Abstracting JP60-162260.
Kinoshita et al., Chem. Abstr. vol. 105 (1986), p. 646, Abstracting JP61-35451.

*Primary Examiner*—Marion E. McCamish
*Assistant Examiner*—Rosemary Ashton
*Attorney, Agent, or Firm*—Wenderoth, Lind & Ponack

[57] ABSTRACT

The present invention provides an electrophotographic photoreceptor consisting essentially of an electrically conductive substrate and a photosensitive layer containing at least one charge transport material selected from the compound shown by formulae (1), (2), (3), (4), and (5):

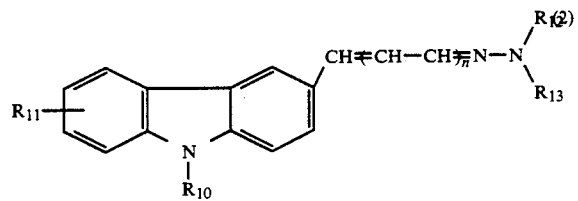

and at least one charge generating material selected from pyrrolopyrrole compounds of formula (6)

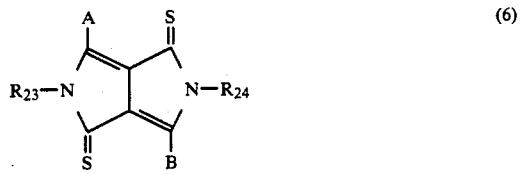

4 Claims, 1 Drawing Sheet

ELECTROPHOTOGRAPHIC PHOTORECEPTORS

The present invention relates to electrophotographic photoreceptors e.g. for laser beam printers, plain paper copiers and combinations thereof, and to novel nitrogen-containing compounds which can be used as charge transport material in electrophotographic photoreceptors.

Various electrophotographic photoreceptors have been suggested, such as those comprising inorganic or organic photoconductive compounds. Particularly in recent years, systems comprising a charge generating material and a charge transport material have been intensively investigated. JP Patent Kokais Sho 59-114 545, Sho 59-228 652, 60-151 645, 60-162 260, 61-35 451 and 63-95 457, and EP Patent Application No. 99 552 disclose electrophotographic photoreceptors comprising diazo pigments as charge generating material in combination with various charge transport materials. Having accomplished a new pyrrolopyrrole type charge generating material, U.S. Pat. No. 4,632,893 discloses an electrophotographic photoreceptor comprising the following compound

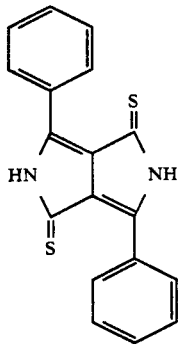

as charge generating material and the hydrazone compound of the following formula

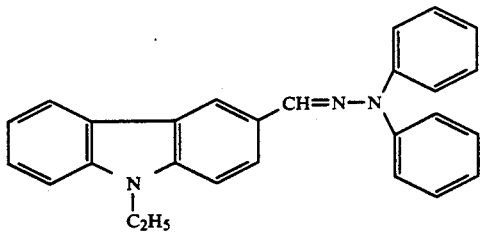

as charge transport material. Although such compositions generally possess good properties, they do not always satisfy modern technological demands.

The purpose of the present invention is therefore to provide an electrophotographic photoreceptor with higher sensitivity and lower residual potential containing a hydrazone and/or enamine compound or a specific nitrogen-containing compound, as well as some new hydrazone compounds which function as an excellent electrophotographic charge transport material when used in combination with a pyrrolopyrrole compound.

Figure 2:
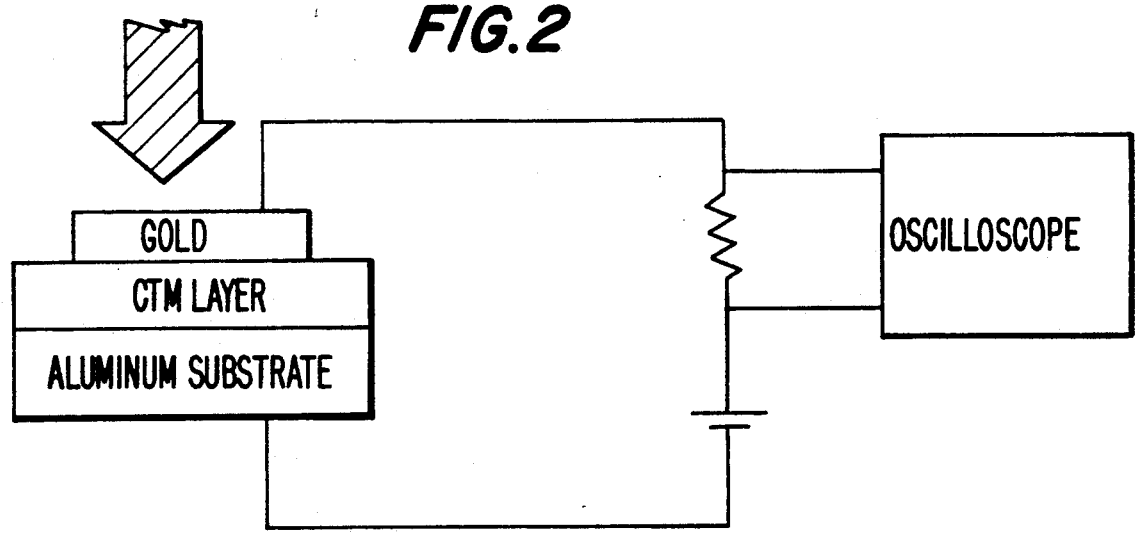

The following is a brief description of the Figures:

FIG. 1: Section view showing an example of a structure of the electrophotographic photoreceptor of the present invention;

FIG. 2: Schematic view showing an example of a set-up for determination of the charge carrier mobility;

The electrophotographic photoreceptor of the present invention has very flat photosensitivity characteristic from the visible light region to the near IR and the material is therefore applicable to both laser beam printers and plain paper copiers as well as combinations of both devices.

A small variation in the chemical structure of the charge transport material surprisingly has a very big effect on the photographic properties of the photosensitive layer. The electrophotographic photoreceptor of the present invention exhibits improved electrophotographic properties, especially higher sensitivity and lower residual potential, compared with the known combination of a hydrazone derivative with a pyrrolopyrrole compound shown in U.S. Pat. No. 4,632,893.

The electrophotographic photoreceptor of the present invention comprises an electrically conductive substrate and a photosensitive layer containing at least one charge transport material selected from the compound of the formulae (1), (2), (3), (4) and (5):

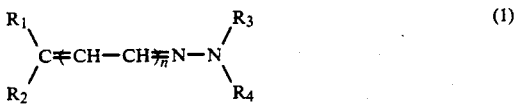

wherein

R$_1$ represents hydrogen, C$_1$-C$_4$alkyl, phenyl or phenyl substituted by halogen, C$_1$-C$_4$alkyl, C$_1$-C$_4$alkoxy, C$_2$-C$_8$-dialkylamino or diaralkylamino of which the ring(s) may have at least one substituent selected from C$_1$-C$_4$alkyl, C$_1$-C$_4$alkoxy, nitro and halogen, R$_2$ represents naphthyl, anthryl or styryl which may be substituted by C$_1$-C$_4$alkyl, C$_1$-C$_4$alkoxy or C$_2$-C$_8$dialkylamino, pyridyl, furanyl, or thiophenyl or a group of formula

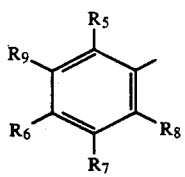

wherein

R$_5$, R$_7$ and R$_9$ represent independently hydrogen, halogen, C$_1$-C$_4$alkyl, C$_1$-C$_4$alkoxy, nitro, hydroxyl, C$_2$-C$_8$dialkylamino, or diphenylamino, R$_6$ represents hydrogen, halogen, C$_1$-C$_4$alkyl, C$_1$-C$_4$alkoxy, nitro, hydroxyl, C$_2$-C$_8$dialkylamino, mono-C$_1$-C$_4$alkyl-monophenylamino or diarylamino or diaralkylamino of which the ring(s) may have at least one substituent selected from C$_1$-C$_4$alkyl, C$_1$-C$_4$alkoxy, nitro and halogen, R$_8$ represents hydrogen, C$_1$-C$_4$alkyl or C$_1$-C$_4$alkoxy, or R$_6$ and R$_7$ jointly form methylendioxy, R$_3$ represents C$_1$-C$_4$alkyl, aryl or aralkyl optionally substituted by C$_1$-C$_4$alkyl, C$_1$-C$_4$alkoxy and/or halogen, $R_4$ represents $C_1$-$C_4$alkyl, aryl or aralkyl optionally substituted by halogen, $C_1$-$C_4$alkyl and/or $C_1$-$C_4$alkoxy, and n represents 0 or 1;

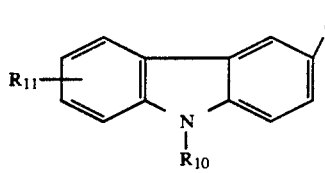

wherein
$R_{10}$ represents $C_1$-$C_4$alkyl which may be substituted by $C_1$-$C_4$alkoxy, aryl, hydroxyl and/or halogen,
$R_{11}$ represents hydrogen, halogen, $C_1$-$C_4$alkyl, $C_1$-$C_4$alkoxy, $C_2$-$C_8$dialkylamino or nitro,
$R_{12}$ represents $C_1$-$C_4$alkyl, aryl which may be substituted by $C_1$-$C_4$alkyl and/or $C_1$-$C_4$alkoxy, or aralkyl,
$R_{13}$ represents $C_1$-$C_4$alkyl, aryl or aralkyl, and
n represents 0 or 1,
provided that, when $R_{10}$ represents ethyl and $R_{11}$ represents hydrogen, $R_{12}$ and $R_{13}$ do not simultaneously represent phenyl;

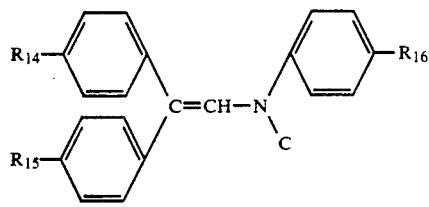

wherein C represents $C_1$-$C_4$alkyl, aralkyl optionally substituted by halogen, $C_1$-$C_4$alkyl or $C_1$-$C_4$alkoxy or a group of the formula

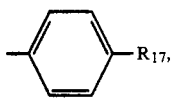

wherein $R_{14}$, $R_{15}$, $R_{16}$ and $R_{17}$ are the same or different and represent hydrogen, $C_1$-$C_4$alkoxy, $C_2$-$C_8$dialkylamino, mono-$C_1$-$C_4$alkyl-monoarylamino, diarylamino or dialkylamino optionally substituted by $C_1$-$C_4$alkyl, $C_1$-$C_4$alkoxy and/or halogen;

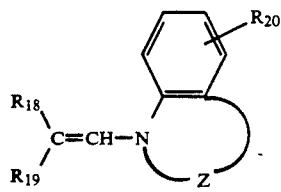

wherein $R_{18}$ is hydrogen, $C_1$-$C_4$alkyl, phenyl or phenyl substituted by $C_1$-$C_4$alkyl, $C_1$-$C_4$alkoxy or $C_2$-$C_8$dialkylamino or containing a methylendioxy bridge, $R_{19}$ is an optionally substituted aryl, or a condensed carbocyclic or heterocyclic aromatic group, $R_{20}$ is hydrogen, $C_1$-$C_4$alkyl, $C_1$-$C_4$alkoxy, optionally substituted aryl or $C_2$-$C_8$dialkylamino, and Z represents an optionally substituted oxygen- or sulfur-containing group which may form a condensed ring with a benzene ring; and

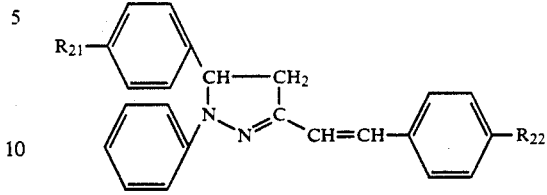

wherein $R_{21}$ and $R_{22}$ independently from each other are hydrogen, $C_1$-$C_4$alkyl, $C_1$-$C_4$alkoxy, mono-$C_1$-$C_4$alkyl-monoarylamino or $C_2$-$C_8$dialkylamino; and at least one charge generating material selected from pyrrolopyrrole compounds of formula (6)

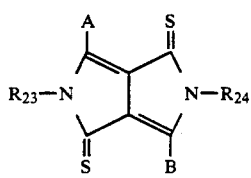

wherein A and B represent independently from each other $C_1$-$C_4$alkyl, aralkyl, cycloalkyl or a carbocyclic or a heterocyclic aromatic radical, and $R_{23}$ and $R_{24}$ represent independently from each other hydrogen or substituents which shall not provide water solubility.

According to the above definitions in the formulae (1) to (5):
examples of $C_1$-$C_4$alkyl, $C_1$-$C_4$alkoxy and $C_2$-$C_8$dialkylamino are e.g. methyl, ethyl, n-propyl, isopropyl, n-butyl and tert-butyl; methoxy, ethoxy, n-propoxy, isopropoxy, n-butoxy and tert-butoxy; dimethylamino, diethylamino, methylethylamino, dipropylamino or dibutylamino;

Mono-$C_2$-$C_4$-alkyl-monophenylamino may be e.g. methyl-phenylamino, ethyl-phenylamino;

Diaralkylamino optionally substituted by $C_1$-$C_4$alkyl or $C_1$-$C_4$alkoxy is e.g. dibenzylamino or di(3-methyl-phenylmethyl)-amino;

Optionally substituted aralkyl is e.g. benzyl, chlorobenzyl;

Halogen in the above formulae is e.g. chlorine or bromine;

$R_6$ and $R_{14}$ to $R_{17}$ as diarylamino may be e.g. diphenylamino;

Optionally substituted aryl is e.g. phenyl, naphthyl, anthryl, bromophenyl, chlorophenyl, methylphenyl, methoxyphenyl, ethoxyphenyl, methyl-ethylaminophenyl, diethylaminophenyl, diphenylaminophenyl, or a group of the formula

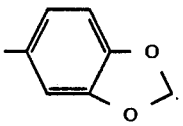

$R_{10}$ as $C_1$-$C_4$alkyl which may be substituted is e.g. methyl, ethyl, n-propyl, n-butyl, chloroethyl, or hydroxyethyl;

Z as optionally substituted oxygen- or sulfur-containing group which may form a condensed ring with a benzene ring is e.g. a group of the following formulae:

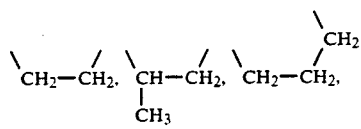

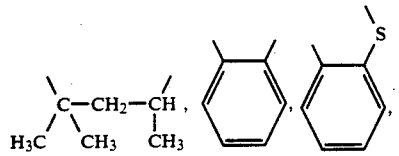

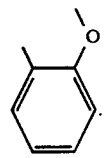

A und B in formula (6) as alkyl groups may be branched, unbranched, saturated or unsaturated, and contain preferably 1 to 18, most preferably 1 to 12, carbon atoms, e.g. methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl or stearyl.

A and B as aralkyl groups are preferably those which contain a preferably mono- or bicyclic aryl radical which is attached through a branched or unbranched alkyl group containing 1 to 6 and preferably 1 to 4, carbon atoms. Examples of such aralkyl groups are benzyl and phenylethyl.

A and B or $R_{19}$ as carbocyclic aromatic radicals are preferably mono- or bicyclic radicals, e.g. phenyl, diphenyl or naphthyl radicals.

A and B or $R_{19}$ as heterocyclic aromatic radicals are preferably mono- to tricyclic radicals. Said radicals may be purely heterocyclic or may contain a heterocyclic ring and one or more fused benzene rings and at least one nitrogen atom, one oxygen atom or one sulfur atom, e.g. pyridyl, furanyl and thiophenyl, or carbazolyl, N-methyl-and N-ethylcarbazolyl.

$R_{23}$ and $R_{24}$ in formula (6) as substituents which do not impart solubility in water are for example branched or unbranched, saturated or unsaturated alkyl groups containing preferably 1 to 18, most preferably 1 to 12, carbon atoms. These groups may be unsubstituted or substituted by hydroxy, halogen, alkoxy or cyano. Examples of such groups are methyl, ethyl, n-propyl, isopropyl, n-butyl, sec-butyl, tert-butyl, tert-amyl, n-pentyl, n-hexyl, allyl, hydroxymethyl, hydroxyethyl, 1,1,3,3-tetramethylbutyl, n-heptyl, n-octyl, nonyl, decyl, undecyl, dodecyl, stearyl, trifluoromethyl, trifluoroethyl or cyanoethyl.

$R_{23}$ and $R_{24}$ may also be aryl groups, preferably unsubstituted phenyl or phenyl substituted by halogen, $C_1$-$C_{12}$alkyl, $C_1$-$C_{12}$alkoxy, $C_1$-$C_{12}$alkylmercapto, trifluoromethyl or nitro.

Those compounds of formula (6) wherein $R_{23}$ and $R_{24}$ are hydrogen are of particular interest.

Preferred compounds of formula (6) are those wherein A and B are identical radicals of formula

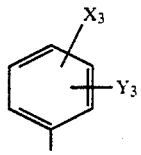

wherein one of the substituents $X_3$ and $Y_3$ is a hydrogen, chlorine or bromine atom, a methyl, cyano, N,N-dimethylamino, N,N-diethylamino, $C_1$-$C_5$alkoxy, $C_1$-$C_5$alkylmercapto or $C_2$-$C_4$alkoxycarbonyl group, and the other substituent is a hydrogen atom. $X_3$ and $Y_3$ are for example in ortho-, meta- or para-position, preferably in meta- or para-position.

Preferred one is the so-called DTPP compound of the formula

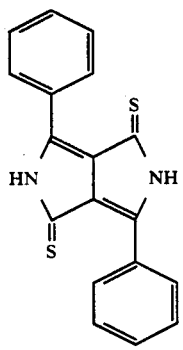

The compounds of formula (6) are described in U.S. Pat. No. 4,632,893 and can be obtained according to the methods described therein.

Preferred charge transport materials are selected from the compounds of formula (1), formula (2), formula (3) and formula (4), wherein:

In formula (1)

$R_1$ represents hydrogen, phenyl or phenyl substituted by $C_1$-$C_4$alkoxy or $C_2$-$C_8$dialkylamino.

$R_2$ represents a group of the following formula

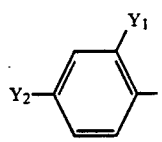

wherein
$Y_1$ represents hydrogen or $C_1$-$C_4$alkoxy and $Y_2$ represents hydrogen, $C_1$-$C_4$alkoxy, methylphenylamino or diphenylamino,
$R_3$ represents phenyl, $R_4$ represents methyl or phenyl, and n represents 0 or 1; in formula (2), $R_{10}$ represents $C_1$-$C_4$alkyl, $R_{11}$ represents hydrogen, $R_{12}$ represents $C_1$-$C_4$alkyl or phenyl, $R_{13}$ represents phenyl, and n represents 0;

in formula (3) C represents methyl, benzyl or a group of formula

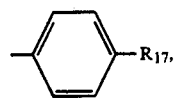

wherein $R_{14}$, $R_{15}$, $R_{16}$ and $R_{17}$ represent independently H or $C_1$-$C_4$alkoxy; and in formula (4) $R_{18}$ and $R_{19}$ are phenyl or phenyl substituted by methoxy, $R_{20}$ is hydrogen and Z is a bridge of formulae —$CH_2CH_2$—,
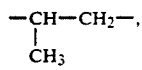
—$CH_2CH_2CH_2$— or
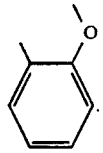
Examples of charge transfer material (CTM) of formula (1), wherein n represents 1, are:
CTM No.
1 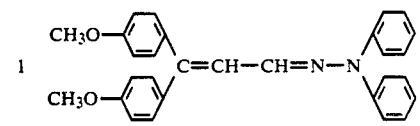
2 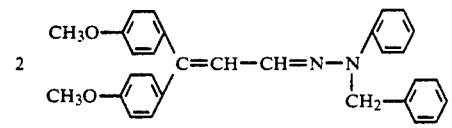
3 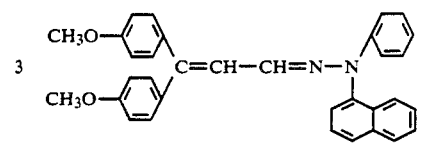
4 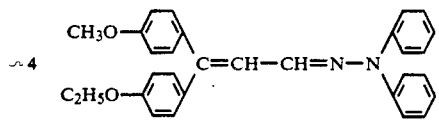
5 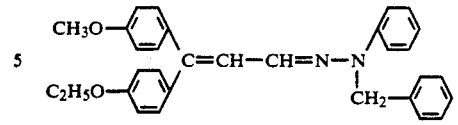
6 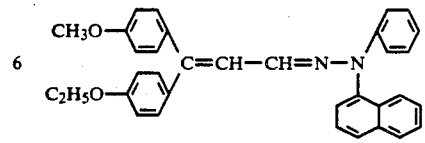
7 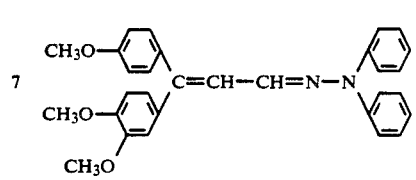
CTM No. -continued
8 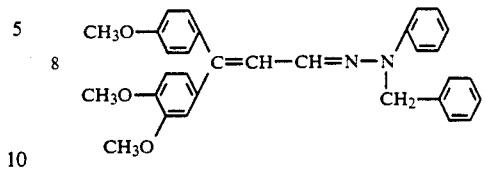
9 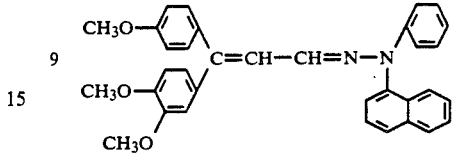
10 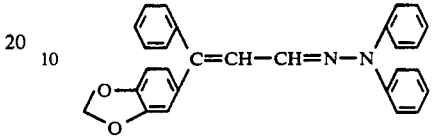
11 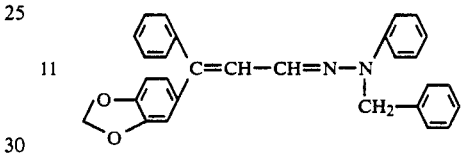
12 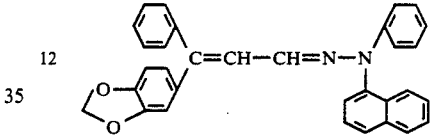
13 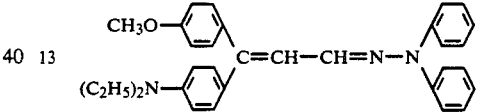
14 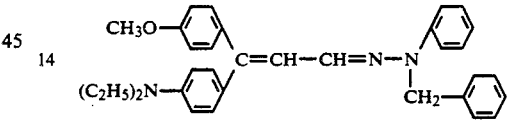
15 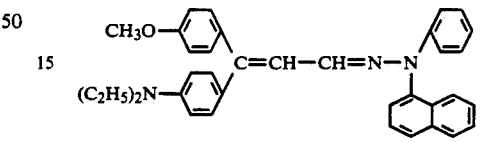
16 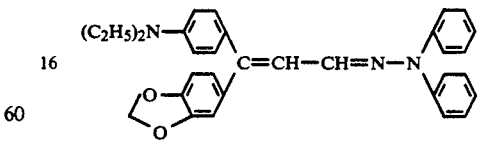
17 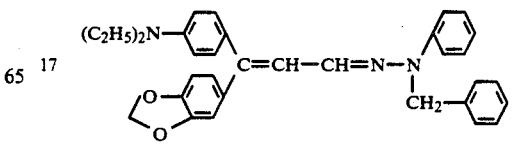

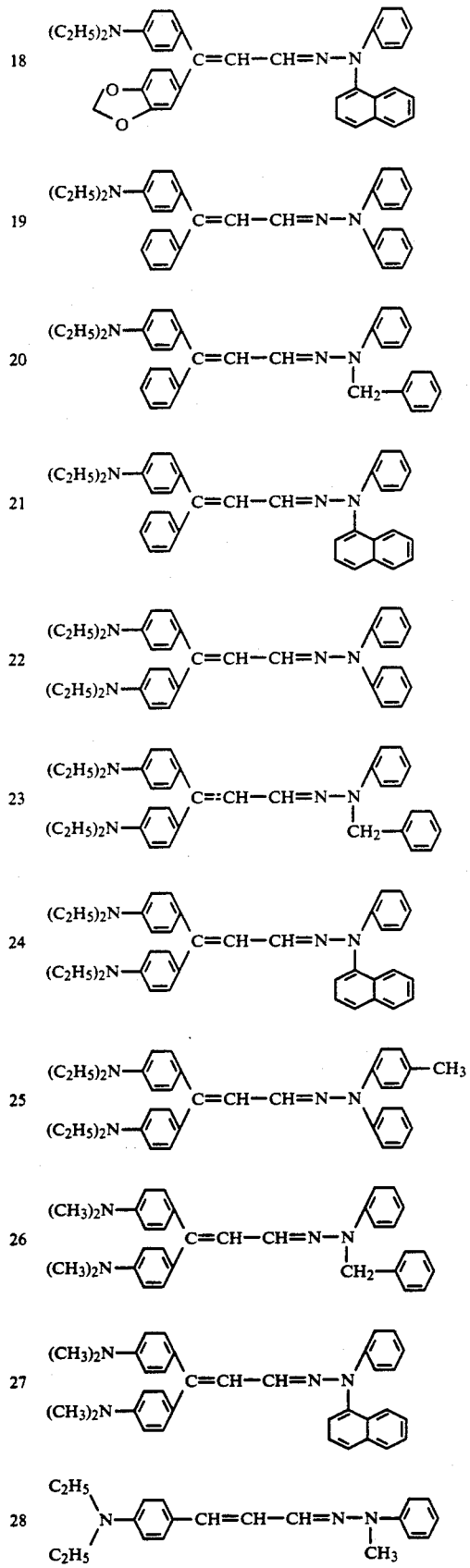
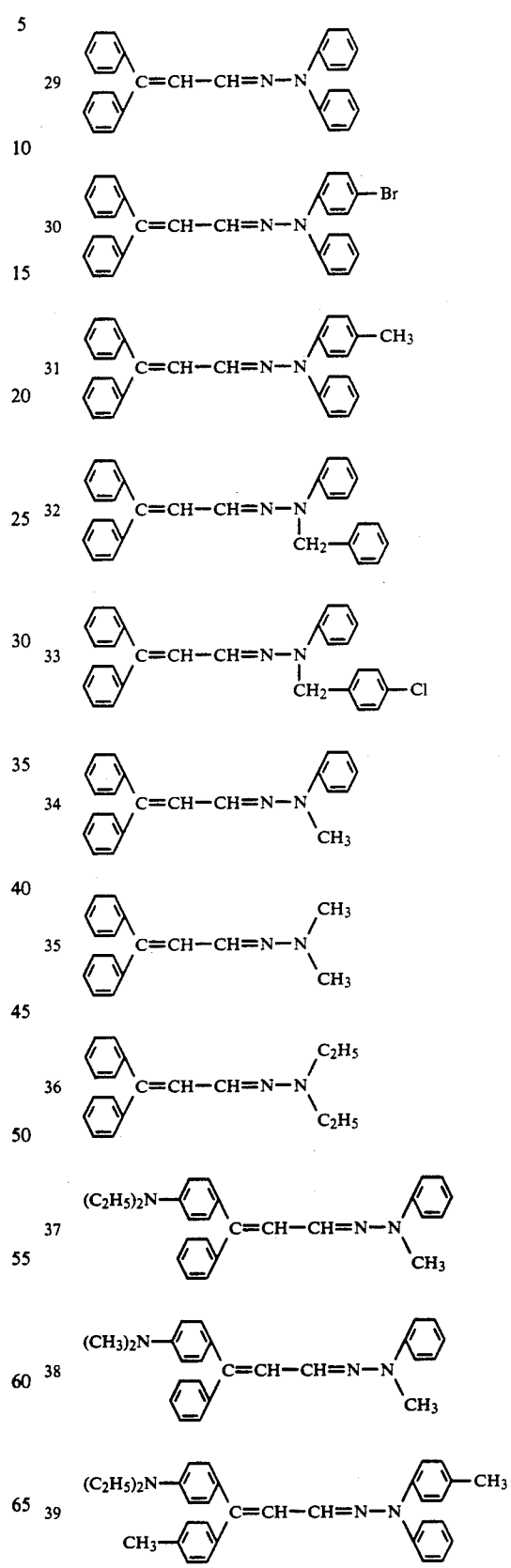

Examples of CTM of formulae (1), wherein n represents 0, are:
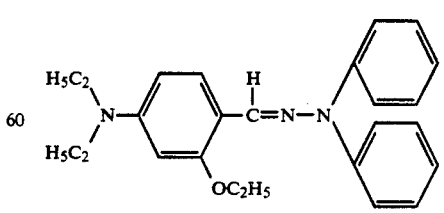

-continued
61 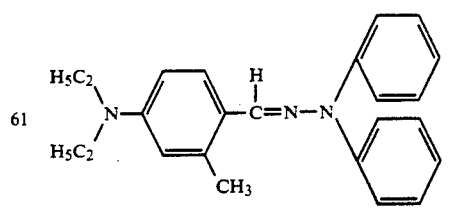
62 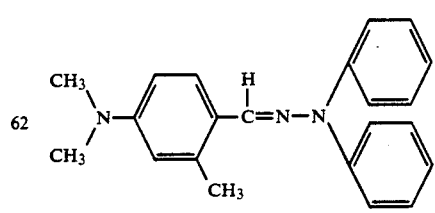
63 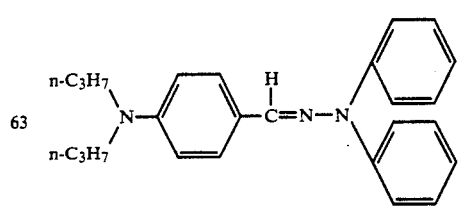
64 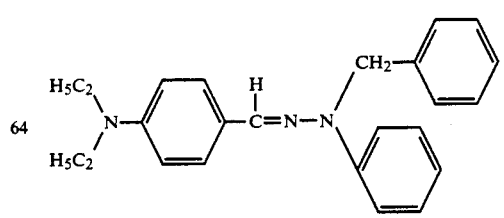
65 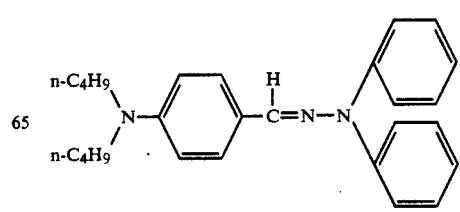
66 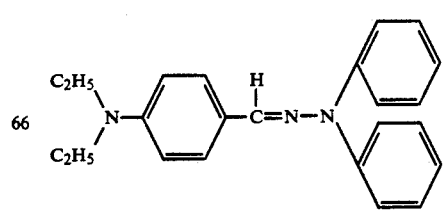
67 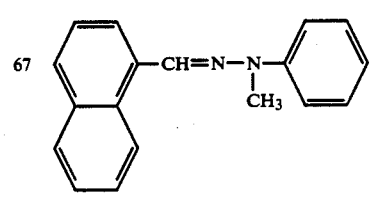
-continued
68 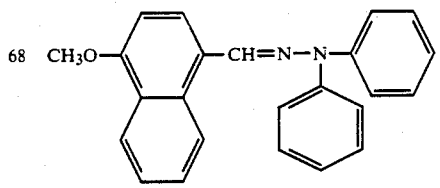
69 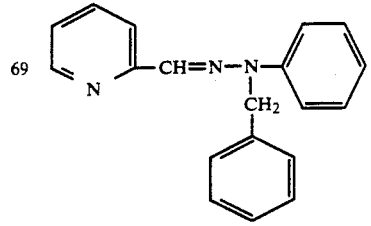
70 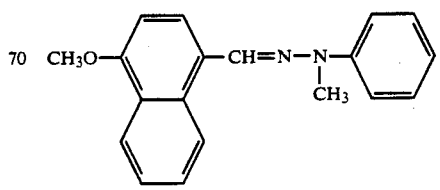
71 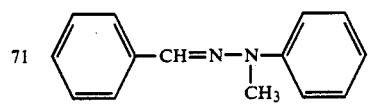
72 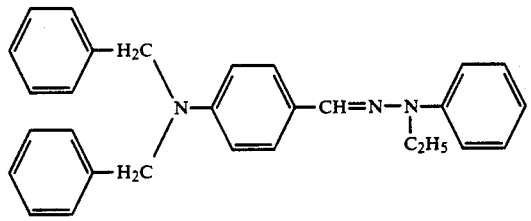
73 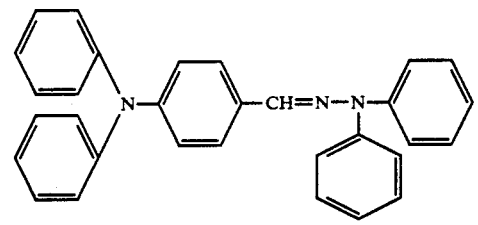
74 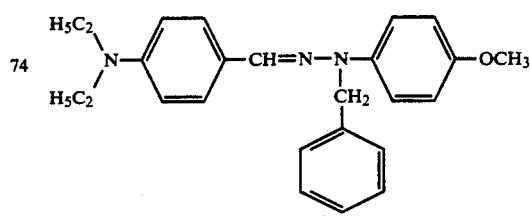
75 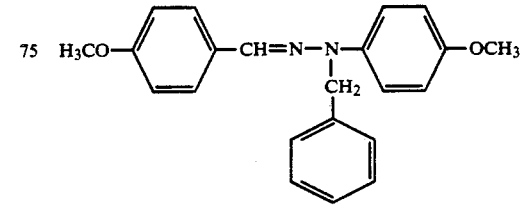

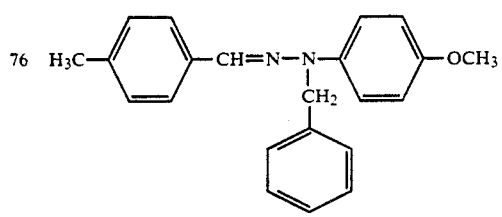
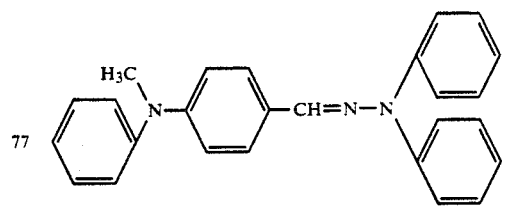
Examples of CTM of formula (2) are:
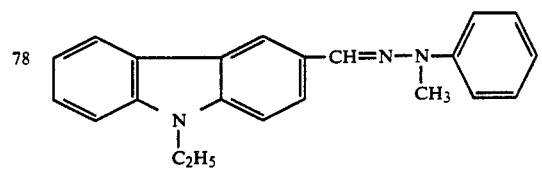
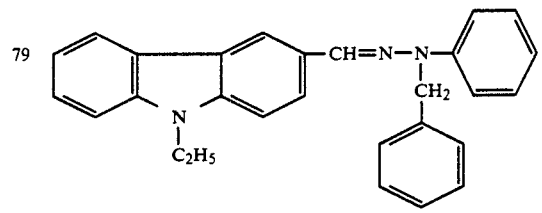
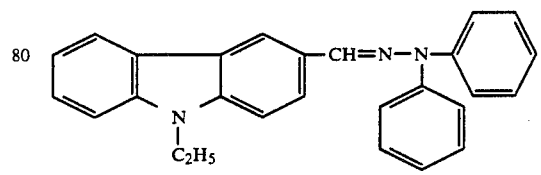
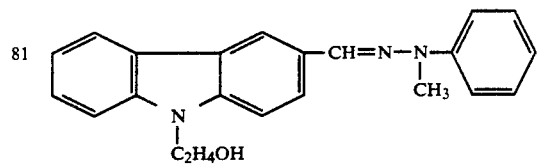
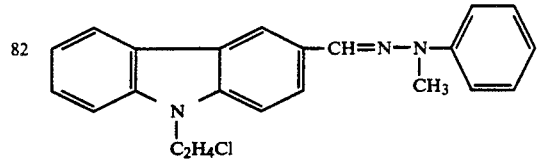
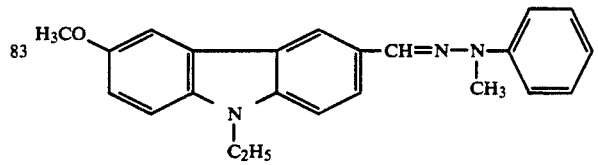
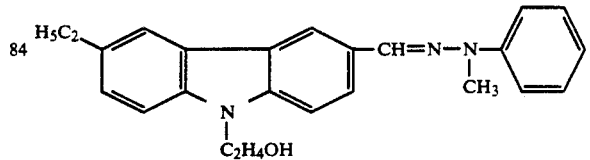

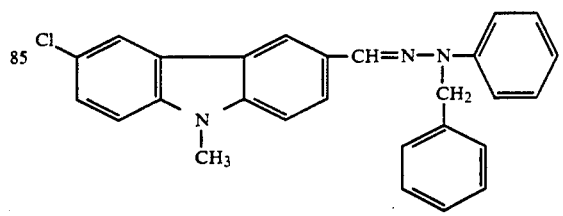
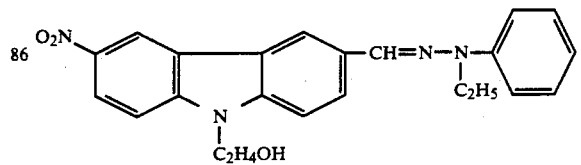
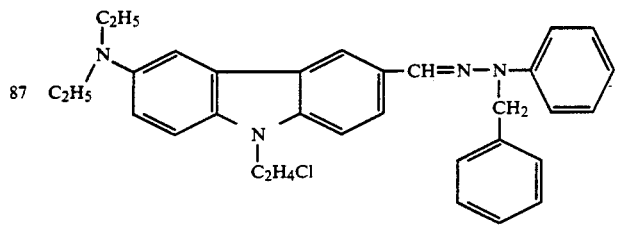
Examples of CTM of formula (4) are:
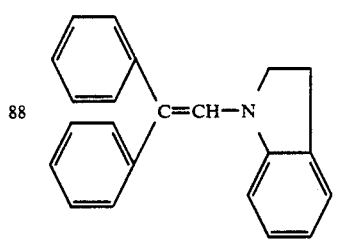
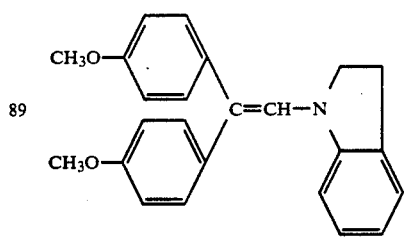
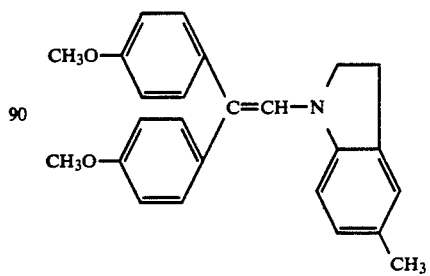
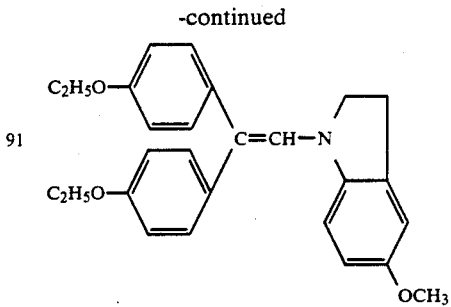
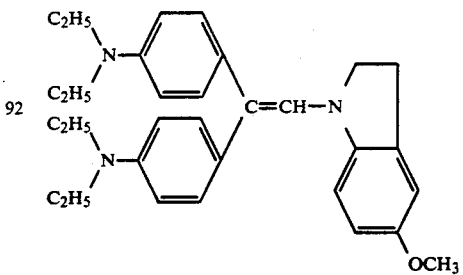
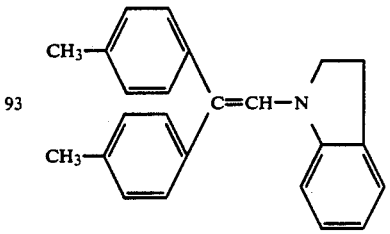

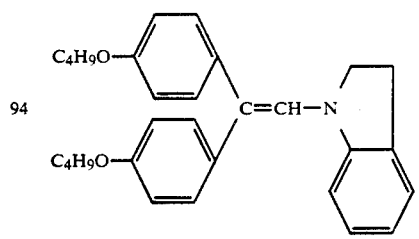
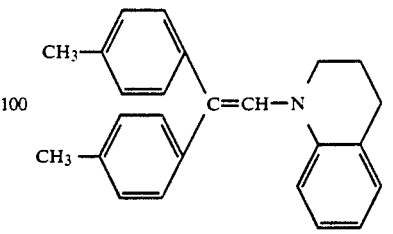
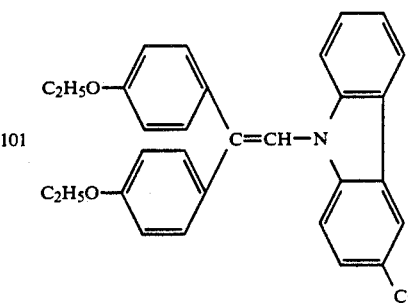
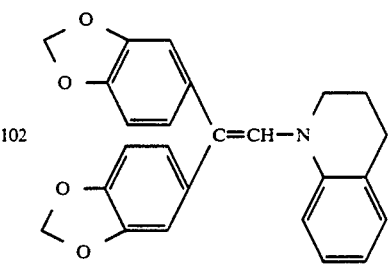
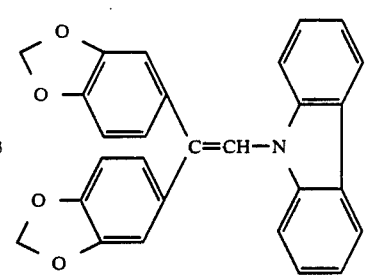
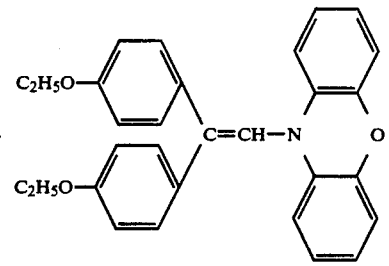
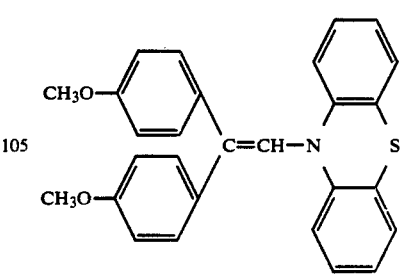

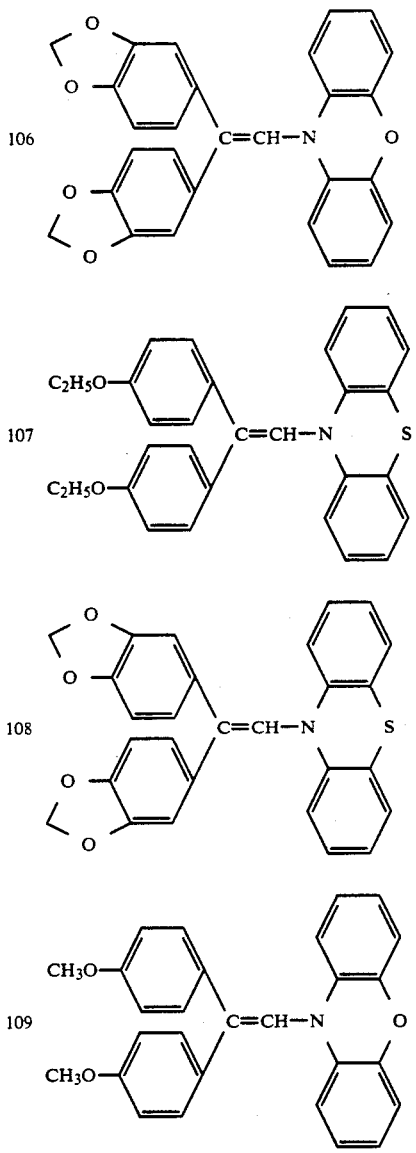
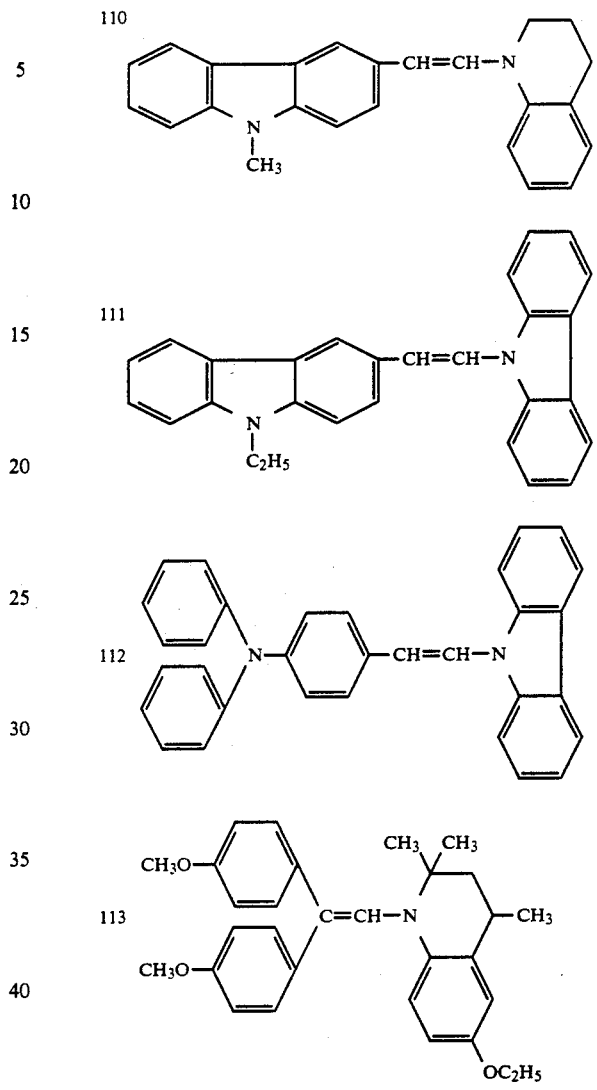
Particularly preferred ones are compounds of the formulae:
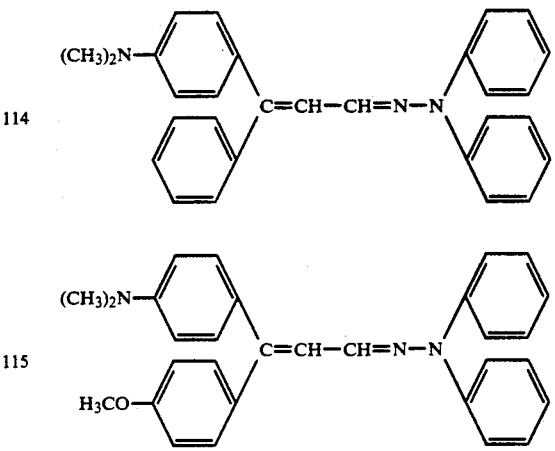

116 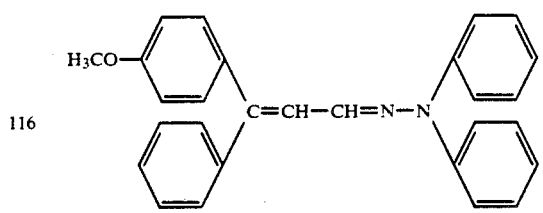
117 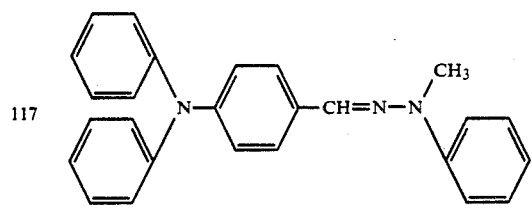
118 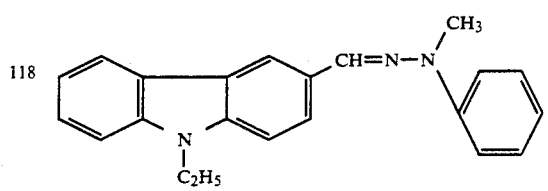
119 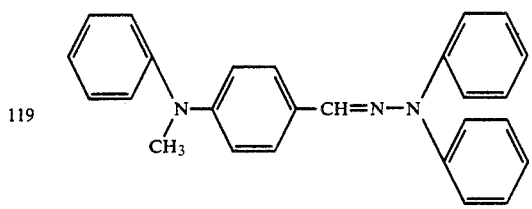
120 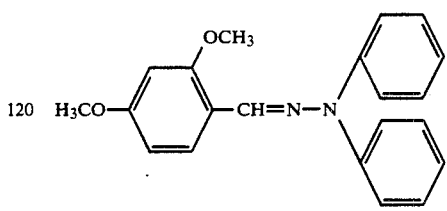
121 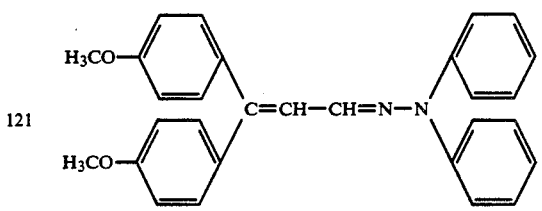
122 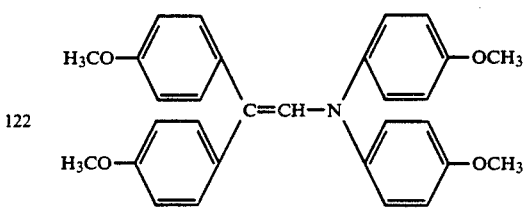

123 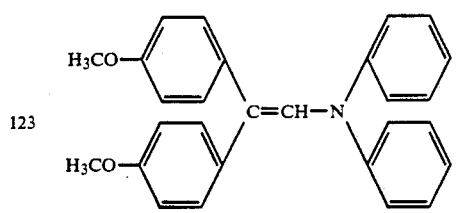
124 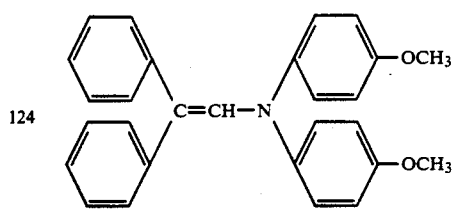
125 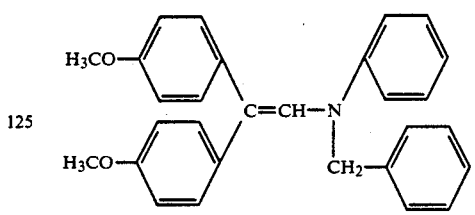
126 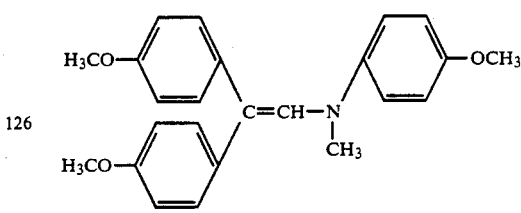
127 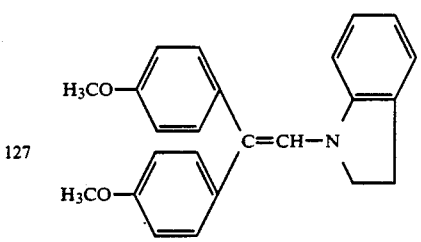
128 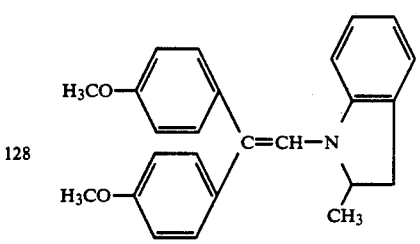
129 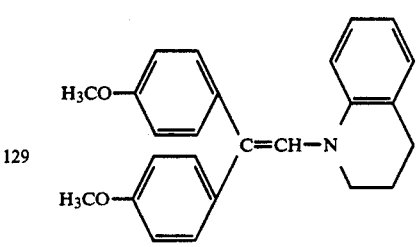

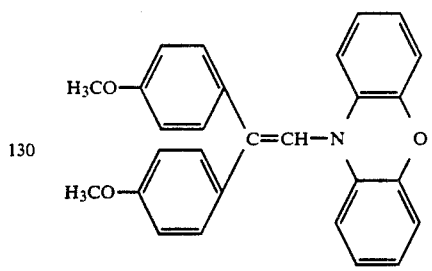

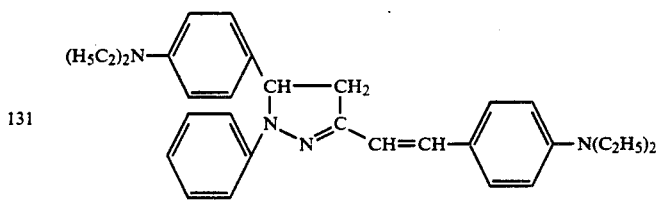

Especially preferred ones are the compounds of formulae:

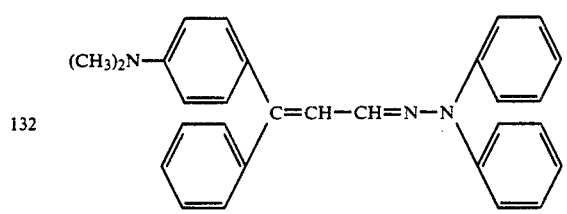

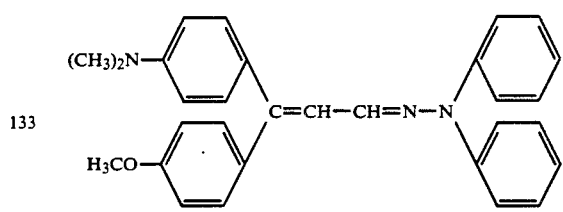

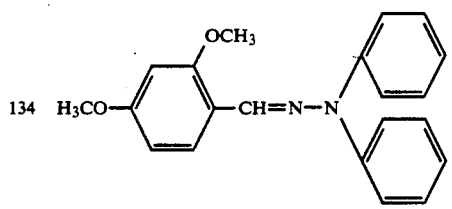

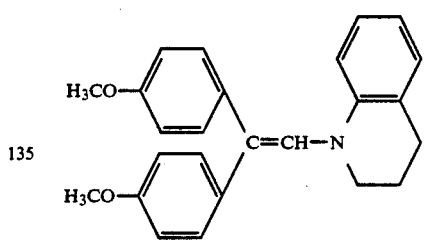

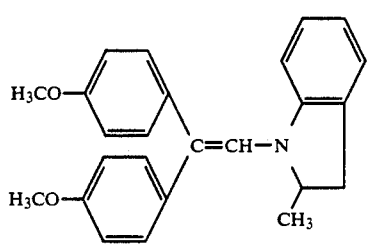 and particularly

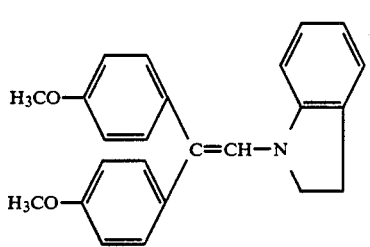

The above compounds Nos. 114, 115 and 120 are novel and also constitute an object of the present invention. They can be prepared from 3-N,N-4'-dimethylaminophenylacrolein, 3-(4'-methoxyphenyl)-3-(4"-dimethylaminophenyl)acrolein and 2,4-dimethoxybenzaldehyde by reacting with a 1,1-diphenylhydrazine salt by a conventional method, respectively.

The compounds of formula (4) are disclosed in JP Patent Kokai-Sho 63-95 457. The compounds of formulae (1), (2), (3) and (5) can be prepared according to known methods e.g. according to JP Patent Kokais Sho 60-162 260 and Sho 59-114 545.

The charge transport materials of formulae (1), (2), (3), (4) and (5) can be used together with other charge transport materials in any amounts provided that the charging property and the photosensitive property are not impaired.

Examples of such compounds are:

hydrazone type compounds other than those shown by formulae (1) and (2), amine derivatives such as 4,4',4'-tris(4-diethylaminophenyl)triphenylamine, nitrogen-containing cyclic compounds such as indole type compounds, oxazole type compounds, isooxazole type compounds, thiazole type compounds, thiadiazole type compounds, imidazole type compounds, pyrazole type compounds, triazole type compounds, condensed polycyclic compounds, pyrazoline type compounds such as 1-phenyl-3-(p-dimethylaminophenyl)pyrazoline, carbazole type compounds such as polyvinyl carbazole, oxadiazole type compounds such as 2,4-di(4-dimethylaminophenyl)-1,3,4-oxadiazole, conjugate type compounds such as 1,1-diphenyl-4,4-bis(4-dimethylaminophenyl)-1,3-butadiene, nitrated compounds such as 2,4,8-trinitrothioxanthone and dinitroanthracene, succinic anhydride, maleic anhydride, dibromomaleic anhydride, fluorenone type compounds such as 2,4,7-trinitro-fluorenone, styryl type compounds such as 9-(4-diethylaminostyryl)anthracene, and tetracyanoethylene.

The pyrrolopyrrole compounds of formula (6) have a low absorption in the NIR-region (near infrared, where the AlGaAs-laser diodes emit light). The NIR-absorption and photoconduction can however be greatly enhance by the method described in U.S. Pat. No. 4,632,893.

The pyrrolopyrrole compounds of formula (6) may be jointly used with other charge generating materials in any ratio that does not adversely affect the photosensitive property.

Examples of such charge generating material may be selenium, selenium-tellurium, amorphous silicon, pyrylium salts, azo type compounds, diazo type compounds, phthalocyanine type compounds, anthanthrone type compounds, perylene type compounds, indigo type compounds, triphenylmethane type compounds, threne type compounds, toluidine type compounds, pyrazoline type compounds, and quinacridone type compounds.

The electrically conductive substrate may be in the form of a plate, drum or sheet which may have rough or pretreated surfaces. The substrate may be made of an electrically conductive material or a electrically non-conductive material covered with an electrically conductive material. Examples of such substrates are aluminum, copper, tin, platinum, titanium, nickel, palladium, indium, their alloys, stainless steel, brass, etc. In the case of aluminum, pretreatment may consist on anodisation. The plastic material which have been vapor-blasted, vacuum deposited or superposed with the above-mentioned metals, glass plates coated with aluminum iodide, tin oxide, indium oxide or indium-tin-oxide (ITO), may be also cited as examples. Preferred substrate is the pretreated aluminum mentioned above.

The photosensitive layer for the electrophotographic photoreceptor of the present invention contains the pyrrolopyrrole compound of formula (6) to generate charge carriers when subjected to exposure, and this material will be used together with the charge transport material of formulae (1), (2), (3), (4) and (5) present in said layer. Such a layer makes it possible, after integral electrostatic charging and imagewise exposure, to produce corresponding latent images which can be visualised by toners.

The photosensitive layer may contain further additives such as conventional sensitizers, plasticizers, deterioration inhibitors such as antioxidants and ultraviolet absorbers and the like.

Examples of the sensitizers may be terphenyl, halogennaphthoquinones and acenaphthylene, quenchers represented by fluorene type compounds like 9-(N,N-diphenylhydrazino)fluorene and 9-carbazolyliminofluorene.

The photosensitive layer may be a mono layer or a multi layer. If the layer is a mono layer, then this contains one or more charge generating materials of formula (6) and one or more charge transport materials of formulae (1), (2), (3), (4) and (5) and an organic binder. In the case of a multi layer, a double layer is the focus of interest, and this double layer comprises a charge generating layer containing one or more pyrrolopyrrole compounds of formula (6) and a charge transport layer containing one or more charge transport materials of formulae (1), (2), (3), (4) and (5) and an organic binder. If the photosensitive layer consists of a mono layer, the mixing ratio of the charge generating material, charge transport material and the binding agent is not critical, but can be determined depending on the characteristics required for a desired electrophotographic photoreceptor.

Electrophotographic photoreceptor of mono layer type can be obtained by preparing a dispersion containing one or more charge generating materials of formula (6) and one or more charge transport materials of formulae (1), (2), (3), (4) and (5) dispersed finely in an organic binder and optionally an organic solvent and applying it onto the above mentioned electrically conductive substrate, drying, removing the solvent, if any, and/or curing it.

Suitable organic solvents are exemplified by aliphatic hydrocarbons such as n-hexene, octane and cyclohexane; aromatic hydrocarbons such as benzene, toluene and xylene; halogenated hydrocarbons such as dichloromethane, dichloroethane, carbon tetrachloride and chlorobenzene; esters such as ethyl acetate and methyl acetate; dimethyl formamide, dimethyl sulfoxide, ethers such as dimethyl ether, diethyl ether, tetrahydrofuran (THF), ethylene glycol dimethyl ether, ethylene glycol diethyl ether and diethylene glycol dimethyl ether; ketones such as acetone, methyl ethyl ketone and cyclohexanone, or mixtures of these solvents.

In the preparation of the dispersion, a leveling agent, surfactant etc. may be added to improve the dispersibility and coating property.

In the case of multi layers, the order of the layers is not critical. For example, the charge transport layer can be prepared on the electrically conductive substrate, and the charge generating layer is then applied thereon, or vice-versa.

The charge generating layer may be formed by vaporizing or sputtering under vacuum the pyrrolopyrrole compound of formula (6) or finely dispersing it in an organic binder, if necessary together with one or more organic solvents. The mixing ratio of the pyrrolopyrrole compound to the binding agent is not critical.

The charge generating layer may jointly contain charge transport materials such as those shown by formulae (1), (2), (3), (4) and (5).

The charge transport layer may be formed by dissolving or finely dispersing the charge transport material of formulae (1), (2), (3), (4) and (5) in one or more organic binders, if necessary together with one or more organic solvents. The mixing ratio of the charge transport material and the binder is not critical.

Electrophotographic photoreceptors of double layer type can be formed by preparing a dispersion of a charge generating layer and a solution or dispersion of a charge transport layer, applying them, in any order desired, on an electrically conductive substrate, drying, removing solvents if any, and/or curing. The organic solvents optionally used for the preparation of the layers may be those mentioned for the single layers. The charge generating layer comprising the pyrrolopyrrole compound of formula (6) may be applied by vaporizing it under vacuum onto the conductive substrate or the charge transport layer as the case may be.

An undercoating layer may be provided between the photosensitive layer and the electrically conductive substrate to enhance their adhesion. For the same purpose, the surface of the conductive substrate can be pretreated with a surface-treating agent such as silane coupling agent, or a titanium coupling agent, etc. The undercoating may consist of natural or synthetic polymer solutions. A surface protecting layer may be formed on the photosensitive layer to protect its surface. Such protecting layers comprise suitable binding agents, deterioration preventing agents, etc.

The binder should be film-forming, insulating and adhesive. Depending on the application, the binder is soluble in organic solvents or in basic mixtures of organic solvents which may also contain water. Particularly suitable binders are those based on polycondensation and polyaddition products such as polyamides, polyurethanes, polyesters, epoxy resins, phenoxy resins, polyketones, polycaarbonates, polyvinyl ketones, polystyrenes, polyvinyl carbazoles, polyacrylamides, polyolefines such as polyethylene, chlorinated polyethylene, or polypropylene, etc., alkyd resins, polysulfons, polyallylate resins, diallylphthalate resins, polyether resins, polymethyl methacrylates, polyvinyl butyrates, polyvinyl chlorides, as well as copolymers such as styrene-acryl copolymers e.g. styrene/maleic anhydride copolymers, styrene/methacrylic acid/methacrylate copolymers, ethylene-vinyl acetate copolymers, vinyl-chloride-vinylacetate copolymers.

The photosensitive layer for the electrophotographic photoreceptor of the present invention contains one or more dithioketopyrrolopyrrole compounds of formula (6) which generate charge carriers when subjected to exposure and which is used together with the charge transport materials of formulae (1), (2), (3), (4) and (5) present in said layers. Such a layered structure makes it possible, after integral electrostatic charging and image-wise exposure, to produce a corresponding latent image which can be visualised by known toners.

Exposure can be effected with light from the visible to the near infrared region. A particular advantage of the dithioketopyrrolopyrroles is that they are also capable of absorbing rays in the near infrared range and that they are also photoconductive in this wave length range. The range of 650 to 850 nm in which gallium arsenide laser diodes operate is of particular interest.

On account of the fact that they exhibit high dark resistance, the dithioketopyrrolopyrroles of formula (6) help to maintain electrostatic potential in unexposed areas.

The invention is illustrated by the following examples.

PREPARATION EXAMPLES OF CHARGE TRANSPORT MATERIALS

EXAMPLE 1

A mixture of 2.5 g of 3-N,N-4'-dimethylaminophenyl-3-phenylacrolein, 2.2 g of 1,1-diphenylhydrazine hydrochloride and 0.82 g of sodium acetate is refluxed for 3 hours in 20 ml of ethanol. After cooling down to room temperature, the crude product is collected by filtration and recrystallized from ethanol. The yield of the resulting compound of the formula

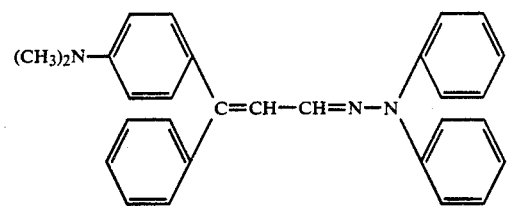

is 2.2 g (48%).
M.W.: 417;
M.P.: 181°–182° C.;
I.P.: 5.45 eV; (I.P=Ionization Potential)
Mass spectrum: M/e 417 (M+).

| Elemental analysis in %: | | | |
|---|---|---|---|
| | H | C | N |
| Found | 6.49 | 83.38 | 10.15 |
| Calculated for C$_{29}$H$_{27}$N$_3$ | 6.52 | 83.42 | 10.06 |

EXAMPLE 2

A mixture of 28 g of 3-(4'-methoxyphenyl)-3-(4''-dimethylaminophenyl)-acrolein, 22 g of 1,1-diphenylhydrazine hydrochloride and 8.2 g of sodium acetate is refluxed for 1 hour in 200 ml of ethanol. After cooling down to room temperature, the crude product is collected by filtration and recrystallized from ethanol-acetone. The yield of the resulting compound of formula

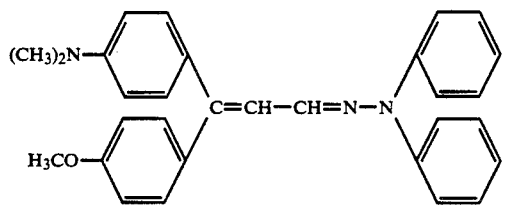

is 23 g (51%).
M.W.: 447;
M.P.: 161°–162° C.;
I.P.: 4.90 eV;
Mass spectrum: M/e: 447 (M+);

| Elemental analysis in %: | | | |
|---|---|---|---|
| | H | C | N |
| Found | 6.55 | 80.32 | 9.35 |
| Calculated for C$_{30}$H$_{29}$ON$_3$ | 6.53 | 80.51 | 9.39 |

EXAMPLE 3

A mixture of 16.6 g of 2,4-dimethoxybenzaldehyde, 22 g of 1,1-diphenylhydrazine hydrochloride and 8.2 g of sodium acetate if refluxed for 1 hour in 150 ml of ethanol. After cooling down to room temperature, the crude product is collected by filtration and recrystallized from ethanol. The yield of the resulting compound of formula

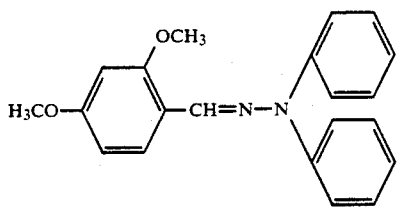

is 24 g (75%).
M.W.: 332;
M.P.: 105°–106° C.;
Mass spectrum: M/e: 332 (M+);

| | Elemental analysis | | |
|---|---|---|---|
| | H | C | N |
| Found | 6.06 | 75.85 | 8.43 |
| Calculated for $C_{21}H_{20}N_2O_2$ | 6.06 | 75.88 | 8.43 |

DETERMINATION OF THE ELECTROPHOTOGRAPHIC CHARACTERISTICS (1) Preparation of sample specimen A tetrahydrofuran solution of CTM/polycarbonate (1 wt./1 wt.) is coated on the charge generating layer film formed on an aluminum substrate (see FIG. 1) and dried.

| Charge transfer layer: (CTL) | CTM/polycarbonate (1/1) of thickness 15 microns |
|---|---|
| Charge generating layer: (CGL) | DTPP film vapour deposited of thickness 1500 Å or less |

AL: Aluminum substrate of thickness 80 microns
(DTPP = dithiodiketopyrrolopyrrole; CTM = charge transfer material).

(2) Electrophotographic characteristics

A sample specimen prepared in the above manner is minus charged at −6.0 KV by means of corona discharge from Electrostatic Paper Analyzer (EPA-8100®, mfd by Kawaguchi Elec. Co.). The surface potential (Vs.p.) is determined first, then the specimen is irradiated with a monochromatic light (800 nm, 5 microW/cm²) from a tungsten-halogen lamp to determine the time when the surface potential reduces to the half value to calculate the half decay exposure E ½. The surface potential at 5 seconds after the exposure is determined to obtain the residual potential. The results are shown in Table 1.

TABLE 1

| | Electrophotographic characteristics | | | |
|---|---|---|---|---|
| Specimen No. | CGM | CTM No. | [1]E½ (μJ/cm²) | [2]Vs.p. (V) | [3]Vr.p. (V) |
| 1 | DTPP | 114 | 0.43 | −377 | −6 |
| 2 | DTPP | 73 | 0.50 | −550 | −10 |
| 3 | DTPP | 115 | 0.35 | −255 | −3 |
| 4 | DTPP | 117 | 0.55 | −656 | −8 |
| 5 | DTPP | 118 | 0.45 | −827 | −23 |
| 6 | DTPP | 120 | 0.45 | −599 | −83 |
| 7 | DTPP | 131 | 0.63 | −590 | −16 |
| 8 | DTPP | 121 | 0.65 | −688 | −31 |
| 9 | DTPP | 119 | 0.65 | −775 | −63 |
| 10 | DTPP | 122 | 0.48 | −353 | −8 |
| 11 | DTPP | 127 | 0.35 | −504 | −7 |
| 12 | DTPP | 123 | 0.53 | −759 | −20 |
| 13 | DTPP | 128 | 0.53 | −771 | −19 |
| 14 | DTPP | 126 | 0.63 | −632 | −31 |

TABLE 1-continued

| | Electrophotographic characteristics | | | |
|---|---|---|---|---|
| Specimen No. | CGM | CTM No. | [1]E½ (μJ/cm²) | [2]Vs.p. (V) | [3]Vr.p. (V) |
| 15 | DTPP | 124 | 0.40 | −620 | −14 |

[1]Half decay exposure
[2]Surface potential
[3]Residual potential
CGM: charge generating material; CTM: charge transfer material Better electrophotographic characteristics are obtained when the surface potential (Vs.p.) is higher, the residual potential (Vr.p.) is lower and the Half Decay Exposure (E ½) is lower.

DETERMINATION OF CARRIER MOBILITY

On an aluminum plate of thickness 80 microns as a substrate conductive layer, a solution comprising 1 part by weight of a charge transport material, 1 part by weight of a polycarbonate resin (Makrolon 2800®), and 8 parts by weight of tetrahydrofuran is coated by means of a wirebar, which is then heated at 60° C. for 5 minutes, and then at 80° C. for 20 minutes to dry out to form a charge transport layer of 15 microns thickness. Then, thin gold film is vapor deposited under vacuum to a thickness of ca. 50 Å as a semi-transparent electrode.

Regarding the layer samples thus obtained, transient photocurrents are evaluated according to the Time-of-Flight method which is disclosed on pages 301–308 of "Solar Cells, 2" (1980) by T. TIEDJE, C. R. WRONSKI, B. ABELES and J. M. CEBULKA, published by Elsevier Sequoia S.A., Lausanne - printed in the Netherlands.

A nitrogen laser pulse (337 nm, 1 nanosecond) is irradiated onto the samples on which an electric field ($10^5$–$10^6$ V/cm) is applied through the gold electrode, and the transit time of the charge carrier from the gold electrode to the aluminum substrate is determined; and carrier mobility is calculated thereby taking the layer thickness and applied electric field into consideration. The experimental set-up for the determination of carrier mobility is schematically illustrated in FIG. 2 and the test results are shown in Table 2.

It is found that the carrier mobility $\mu$ (cm²/Vsec) correlates to the strength of electric field E (V/cm) in accordance with the following equation:

$$\log \mu = a \times E + b \quad (a, b = \text{constant})$$

Below, the constant values for a, b and the carrier mobilities with an applied voltage of 500 V (electric field $3.33 \times 10^5$ V/cm) are tabulated.

TABLE 2

| CTM No. | a | b | Carrier mobility (cm²/V sec) at 3.33 × $10^5$ V/cm of fieldstrength |
|---|---|---|---|
| 66 | $1.99 \times 10^{-6}$ | −5.95 | $51.6 \times 10^{-6}$ |
| 73 | $6.89 \times 10^{-7}$ | −5.07 | $5.02 \times 10^{-6}$ |
| 114 | $1.99 \times 10^{-6}$ | −6.13 | $3.41 \times 10^{-6}$ |
| 115 | $1.77 \times 10^{-6}$ | −6.28 | $2.04 \times 10^{-6}$ |
| 117 | $1.46 \times 10^{-6}$ | −5.14 | $2.22 \times 10^{-5}$ |
| 118 | $1.55 \times 10^{-6}$ | −6.22 | $1.98 \times 10^{-6}$ |
| 119 | $1.83 \times 10^{-6}$ | −5.58 | $1.07 \times 10^{-5}$ |
| 120 | $1.47 \times 10^{-6}$ | −6.41 | $1.20 \times 10^{-6}$ |
| 121 | $1.47 \times 10^{-6}$ | −5.87 | $4.16 \times 10^{-6}$ |
| 122 | $8.36 \times 10^{-7}$ | −5.73 | $3.53 \times 10^{-6}$ |
| 123 | $9.27 \times 10^{-7}$ | −6.02 | $1.94 \times 10^{-6}$ |
| 124 | $1.16 \times 10^{-6}$ | −5.20 | $1.54 \times 10^{-5}$ |
| 126 | $1.13 \times 10^{-6}$ | −6.20 | $1.50 \times 10^{-6}$ |

TABLE 2-continued

| CTM No. | a | b | Carrier mobility (cm$^2$/V sec) at $3.33 \times 10^5$ V/cm of fieldstrength |
|---|---|---|---|
| 127 | $8.93 \times 10^{-7}$ | −5.83 | $2.93 \times 10^{-6}$ |
| 128 | $1.14 \times 10^{-6}$ | −5.84 | $3.46 \times 10^{-6}$ |

As illustrated in above Tables 1 and 2, the tested combinations show good or improved sensitivity (E ½), surface potential and residual potential as compared to the prior art combinations.

What is claimed is:

1. Electrophotographic photoreceptor consisting essentially of an electrically conductive substrate and a photosensitive layer containing at least one charge transport material selected from the group consisting of the compounds of the formulae

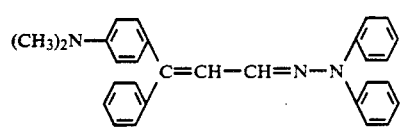
114

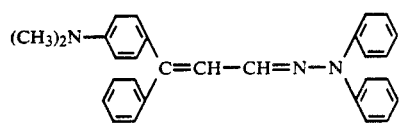
115

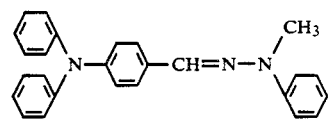
117

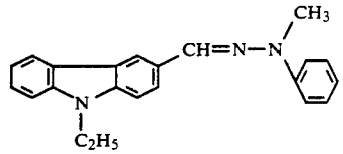
118

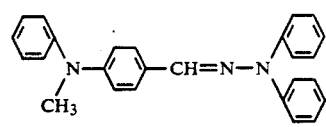
119

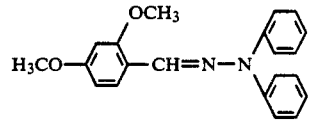
120

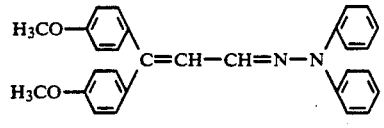
121

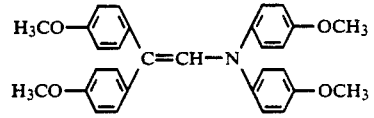
122

-continued

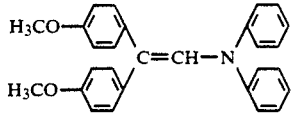
123

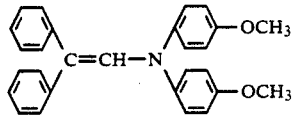
124

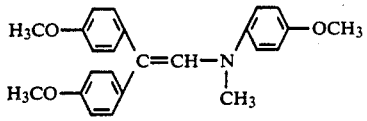
126

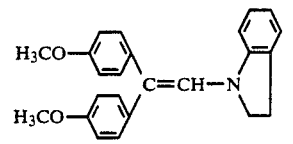
127

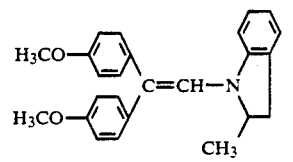
128

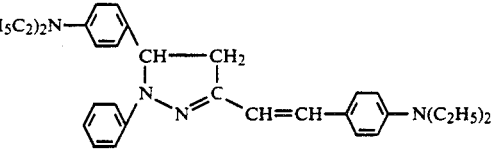
131

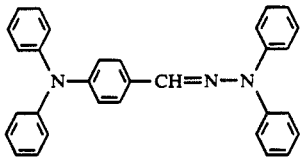
73

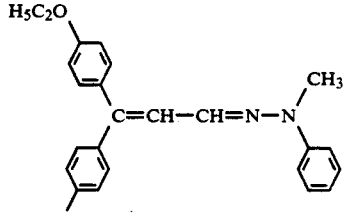
44

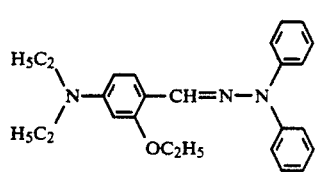
60

-continued

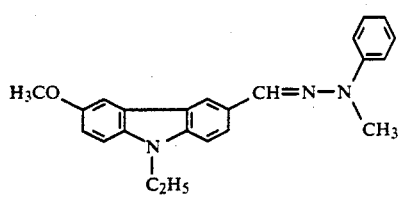
83 and at least one charge generating material selected from pyrrolopyrrole compounds of formula (6)

(6)

wherein

A and B represent independently from each other $C_1$-$C_4$alkyl, aralkyl, cycloalkyl or a carbocyclic or heterocyclic aromatic radical, and $R_{23}$ and $R_{24}$ represent independently from each other hydrogen or substituents which shall not provide water solubility.

2. Electrophotographic photoreceptor according to claim 1, wherein the charge generating material has the formula

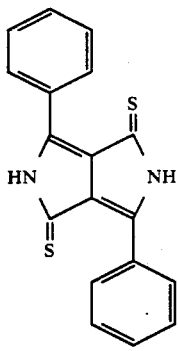

3. Electrophotographic photoreceptor according to claim 1, wherein the charge transport material has the formula

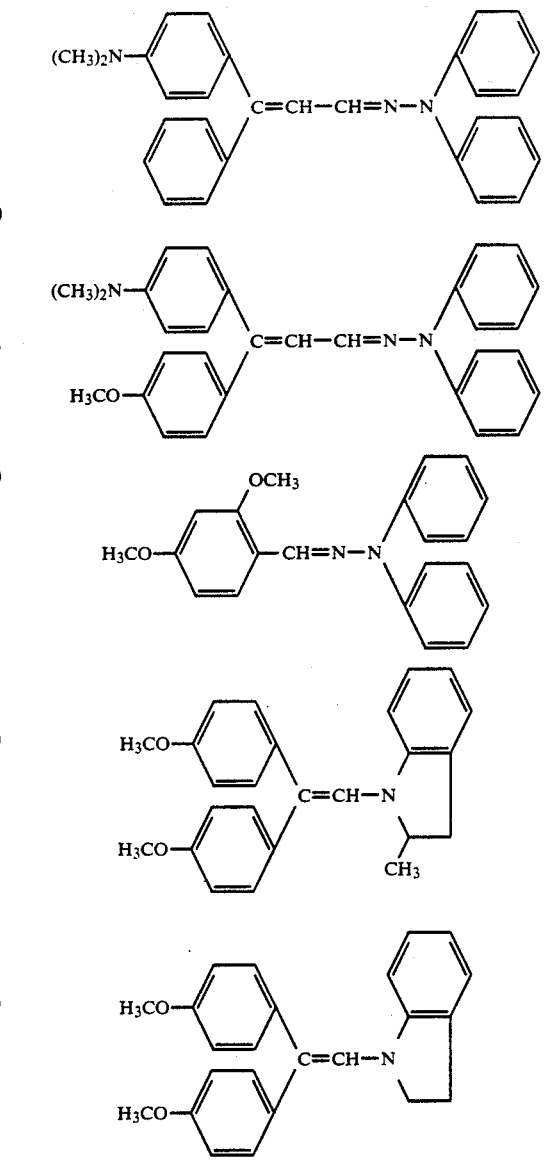

4. A composition for electrophotographic photoreceptor containing at least one charged transport material as defined in claim 1, and at least one charge generating material as defined in claim 1.

* * * * *

UNITED STATES PATENT AND TRADEMARK OFFICE
CERTIFICATE OF CORRECTION

PATENT NO. : 5,098,810

DATED : March 24, 1992

INVENTOR(S) : JIN MIZUGUCHI, SEIJI HOMMA, HIROSHI YAMAMOTO, TAKASHI DENO

It is certified that error appears in the above-identified patent and that said Letters Patent is hereby corrected as shown below:

Column 35, correct formula 115 appearing at line 30 to read as follows:

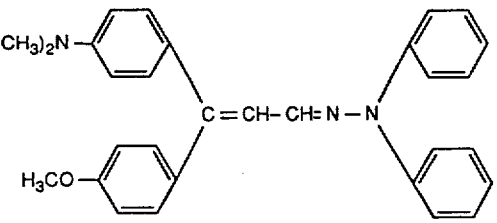

Signed and Sealed this

Twenty-third Day of June, 1998

Attest:

BRUCE LEHMAN

*Attesting Officer*     Commissioner of Patents and Trademarks